United States Patent
Hosokawa et al.

[11] Patent Number: 5,247,560
[45] Date of Patent: Sep. 21, 1993

[54] APPARATUS AND METHOD OF MEASURING BONE MINERAL DENSITY AND BONE STRENGTH

[75] Inventors: Yoshinori Hosokawa, Tanabe; Haruyoshi Hirata, Kyoto, Japan

[73] Assignee: Horiba, Ltd., Kyoto, Japan

[21] Appl. No.: 875,667

[22] Filed: Apr. 29, 1992

[30] Foreign Application Priority Data

May 3, 1991 [JP] Japan .................................. 3-130630

[51] Int. Cl.⁵ ............................................. G01B 15/02
[52] U.S. Cl. ........................................ 378/54; 378/51; 378/89; 378/90
[58] Field of Search .................. 378/51, 54, 56, 58, 378/70, 71, 86, 88, 89, 90

[56] References Cited

U.S. PATENT DOCUMENTS 4,123,654 10/1978 Reiss et al. .............................. 378/90
4,228,351 10/1980 Snow et al. .............................. 378/90

Primary Examiner—David P. Porta
Attorney, Agent, or Firm—Price, Gess & Ubell

[57] ABSTRACT

A highly reliable apparatus and method of measuring bone mineral density and bone strength simultaneously is provided. Pleochromatic X-rays emitted from an X-ray tube are incident upon an object to be measured. Transmitted X-rays and diffracted X-rays, generated during the time period when the X-rays are passed through the object, are separately detected to simultaneously measure the bone mineral density and the bone strength.

12 Claims, 4 Drawing Sheets (A)

(B)

APPARATUS AND METHOD OF MEASURING BONE MINERAL DENSITY AND BONE STRENGTH

BACKGROUND OF THE INVENTION

1. Field of the Invention

The present invention relates to an apparatus and method of measuring bone mineral density and bone strength and, more particularly, to the use of pleochromatic X-rays for such measurements.

2. Description of Related Art

A method of diagnosing osteoporosis and renal osteodystrophy of dialysis patients, by, for example, measuring the bone mineral density, is known in the prior art. As shown in FIG. 5, an X-ray tube 31 receives power from a stabilized power source for applying an appointed voltage to the X-ray tube 31. The resulting X-rays are filtered by an X-ray filter 33, and collimated by a primary collimator 34. A support 35 for supporting an object 36 to be measured locates the object 36 adjacent an X-ray detector 38. A secondary collimator 37 finally defines the path of the transmitted X-rays 42 through the object. The resulting measurement signals can be processed by a signal-treating portion 39.

In the above-described construction white (continuous) X-rays 40, emitted from the X-ray tube 31, are turned into monochromatic secondary X-rays 41 by passing through the X-ray filter 33. They are then incident upon the object to be measured, for example, a waist portion of the human body, through the primary collimator 34. The incident secondary X-rays 41 are transmitted through the object to be measured 36 and, while being absorbed by bone material in the object result in the transmitted X-rays 42. The transmitted X-rays 42 are detected by the X-ray detector 38 through the secondary collimator 37. The detected signal is treated in the signal-treating portion 39.

A NaI (Tl) scintillator, a CdWO$_4$ scintillator, a CdTe semiconductor detector and the like has been used as the X-ray detector 38 so that only the transmitted X-rays 42, which have passed through the object to be measured 36, can be detected. As a result, although data on the bone mineral density (quantity of bones) are obtained, data on the bone strength (condition of bones), indicating a content of crystalline ingredients in the bones, cannot be obtained. Thus, the bone strength has been estimated from the data on the bone mineral density, and the above described diagnosis has not always been accurate.

The prior art is still seeking to optimize the measurement of bone mineral density and bone strength.

SUMMARY OF THE INVENTION

An object of the present invention is to provide a highly reliable method and apparatus capable of separately measuring bone mineral density and bone strength. In order to achieve an improved method of measuring bone mineral density and bone strength, X-rays emitted from an X-ray tube are pleochromatically filtered to be incident upon an object to be measured. Transmitted X-rays and diffracted X-rays, generated during a time period when the X-rays are passing through the object to be measured, are separately detected to simultaneously measure the bone mineral density and the bone strength.

The method of measuring both bone mineral density and bone strength includes the following steps of:

applying a stream of X-rays from a source to a target capable of generating pleochromatic X-rays;

forming the pleochromatic X-rays into a predetermined measurement beam having an optical axis;

applying the measurement beam to a bone target;

dividing the transmitted X-rays into a first group along the optical axis and a second group off of the optical axis;

measuring the X-rays transmitted through the bone target along the optical axis to provide a first measurement signal;

measuring the X-rays diffracted off of the optical axis to provide a second measurement signal;

processing the first measurement signal to provide an indication of bone mineral density, and processing the second measurement signal to provide an indication of bone strength.

Preferably, at least a pair of different wavelengths are transmitted along the optical axis to compensate for the effect of tissue. Additionally, a wave discriminating circuit can discriminate between the first and second measurement signals on the basis of their wavelengths.

According to the improved method of the present invention, the transmitted X-rays and the diffracted X-rays can be quantitatively determined discriminatively, so that the bone mineral density and the bone strength can be separately and simultaneously measured. Thus, highly reliable measurements can be obtained.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide an improved apparatus and method of measuring bone mineral density and bone strength.

Figure 1:
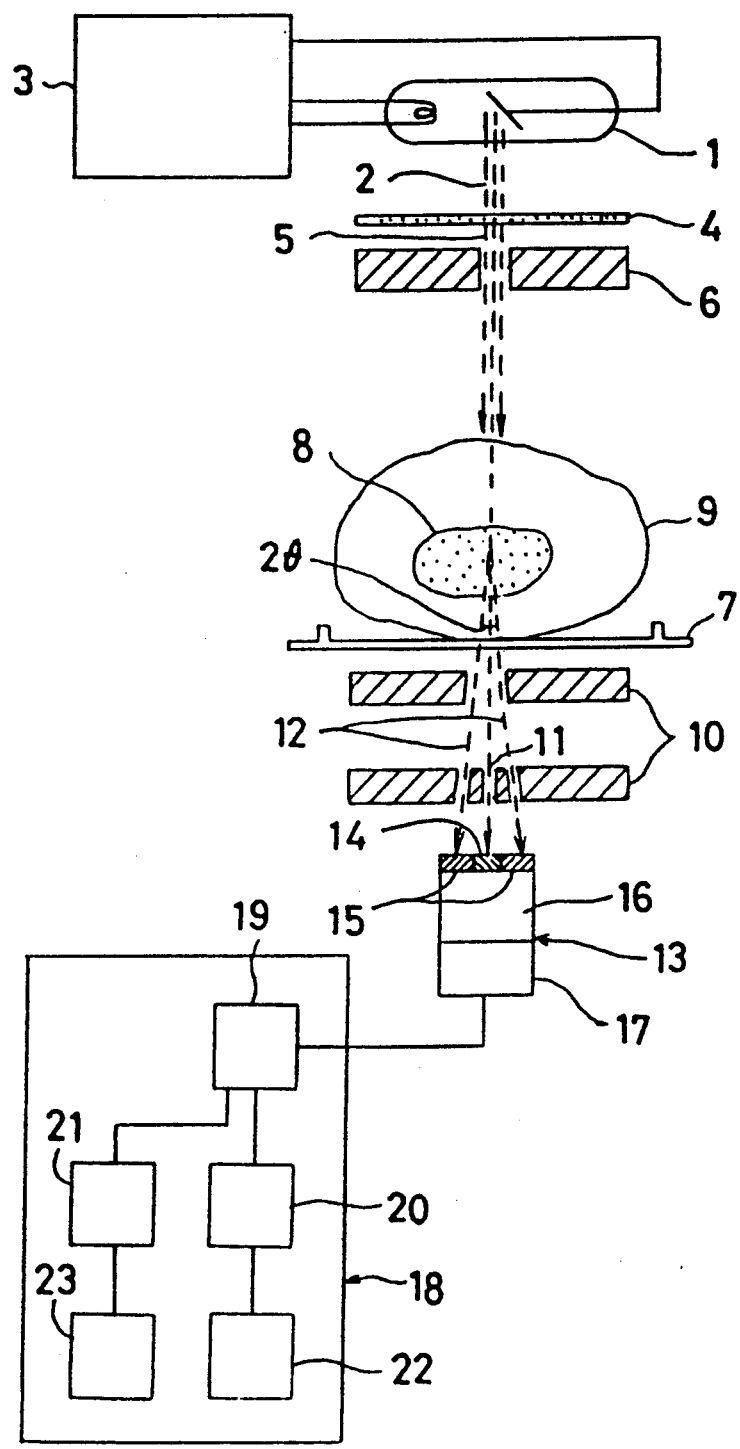
FIG. 1 is a schematic drawing showing an apparatus for applying a method of measuring bone mineral density and bone strength according to the present invention.

FIG. 1 discloses the construction of a first embodiment for putting a method of measuring bone mineral density and bone strength into practice. Referring to FIG. 1, reference numeral 1 designates an X-ray tube emitting white X-rays 2. An output of the X-ray tube 1 is controlled by a stabilized power source 3 to prevent any fluctuating. Reference numeral 4 designates an X-ray filter adapted to turn the white X-rays 2 into pleochromatic X-rays 5, having, for example, at least two different wavelengths. Separation occurs as a result of a K-absorption edge of elements in the X-ray filter 4 and the incident radiation is changed into secondary X-rays by the target.

Reference numeral 6 designates a primary collimator for focusing the secondary X-rays 5 into beam-flux, having a suitable predetermined diameter for the particular target. Reference numeral 7 designates a support (transparent to the X-rays) for supporting a target object 9 to be measured, including a bone 8, such as a wrist portion of the human body. The bone is surrounded by soft tissue and muscle. Reference numeral 10 designates a secondary collimator for preventing scattered X-rays, which are generated when the beam-flux of the secondary X-rays 5 is incident upon the object 9 to be measured, or brought into collision with surrounding substances, from being incident upon an X-ray assembly detector 13, which will be mentioned later. The secondary collimator 10 is a pair of spaced plates with a beveled aperture in the first plate and a plurality of apertures in the second plate.

The above-described construction has certain components similar to a conventional apparatus of this type. A part of the secondary X-rays 5 travel in a straight line along the optical axis and are absorbed partially by the bone 8 included in the object 9 to be measured. Another portion of the secondary X-rays 5 are diffracted by crystals in the bone 8.

The X-rays that travel along the straight path or optical axis of the emission from the X-ray tube 1 are subject to absorption by both the bone and soft tissue. Preferably, at least two different wavelengths of X-rays having different absorption coefficients to both the bone and soft tissue mass are used in order to determine the bone density as follows.

Thus, if the two wavelengths are A keV X-rays and B keV X-rays and when:

$I_0^A$: A keV Incident ray intensity
$I_0^B$: B keV Incident ray intensity
$I^A$: A keV Transmission ray intensity
$I^B$: B keV Transmission ray intensity
$\mu_S^A$: Absorption coefficient of A keV to soft tissue mass (cm$^2$/g)
$\mu_S^B$: Absorption coefficient of B keV to soft tissue mass (cm$^2$/g)
$\mu_B^A$: Absorption coefficient of A keV to bone mass (cm$^2$/g)
$\mu_B^B$: Absorption coefficient of B keV to bone mass (cm$^2$/g)
$M_S$: Soft tissue density (g/cm$^2$)
$M_B$: Bone density (g/cm$^2$)

the following equations are obtained:

$$I^A = I_0^A \exp(-\mu_S^A M_S - \mu_B^A M_B)$$

$$I^B = I_0^B \exp(-\mu_S^B M_S - \mu_B^B M_B)$$

$M_B$ is thus obtained as follows:

$$M_B = \frac{\frac{\mu_S^A}{\mu_S^B} \cdot \ln \frac{I^B}{I_0^B} - \ln \frac{I^A}{I_0^A}}{\mu_B^A - \frac{\mu_S^B}{\mu_S^B} \cdot \mu_B^B}$$

The X-rays 12 that are diffracted by the crystal lattice structure of the bone 8 deviate from the optical axis and after passing through the outer aperture in the second plate contact a detector. The diffractor X-rays 12 are diffracted so as to meet 2d sin $\theta = \lambda$ (wherein d represents a face interval of crystal lattice, $\theta$ represents a diffraction angle, $\lambda$ represents a wavelength).

Figure 2:
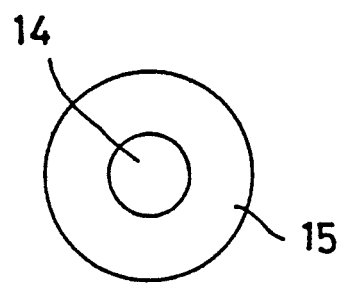
FIG. 2 is a plan view showing the relationship of a pair of scintillators.

Thus, in this preferred embodiment, a NaI (Tl) scintillator 14 and a CsI (Tl) scintillator 15 are concentrically arranged at a central portion and on a circumference, respectively, of the front surface of the X-ray detector assembly 13. The X-rays contact the detector and provide a luminescence of a wavelength characteristic of the material of the detector. The X-ray detector assembly 13 is disposed on the downstream side of the secondary collimator 10. The NaI (Tl) scintillator 14 and the CsI (Tl) scintillator 15 are optically connected with a photo multiplier 16 and a preamplifier 17. The preamplifier 17 is arranged on the downstream side of the photo multiplier 16 for converting a current signal into a voltage signal, as shown in FIG. 2, so that the transmitted X-rays 11 and the diffracted X-rays 12 may be incident upon the NaI (Tl) scintillator 14 and the CsI (Tl) scintillator 15, respectively.

Reference numeral 18 designates a signal-treating portion for treating a detected signal put out from the X-ray detector assembly 13. The signal-treating portion 18 comprises, for example, a conventional wave shape-discriminating circuit 19, counting circuits 20, 21, and operating circuits 22, 23. As can be readily appreciated, the operating circuits can include a microprocessor system with an appropriate reflective algorithm to perform known computations.

The scintillation light from NaI (Tl) and CsI (Tl) are divided through the wave-shape-discriminating circuit 19 as the outputs of the preamplifier 17 and correspondingly measured by the counting circuits 20 and 21.

The wave shape discriminating circuit 19 can include a linear amplifier circuit, such as a model 460 Ortec, connected in parallel to a pair of delay amplifier circuits, such as Tennelec models Tc-215, and a pair of pulse shape analyzer circuits, such as Ortec model 552. Each of these circuit chips are appropriately connected as inputs to a dual linear gate, such as a Tennelec model Tc310, which in turn has outputs connected to a linear router circuit, Tennelec model Tc-306. The outputs are appropriately connected to the counting circuits 20 and 21.

The light source 1, the X-ray filter 4, the primary collimator 6, the secondary collimator 10, and the X-ray detector 13 are also adapted to be movable in a horizontal direction by means of a scanning drive mechanism (not shown), respectively. Thus, the entire bone mass can be scanned to determine both density and strength.

Figure 3:
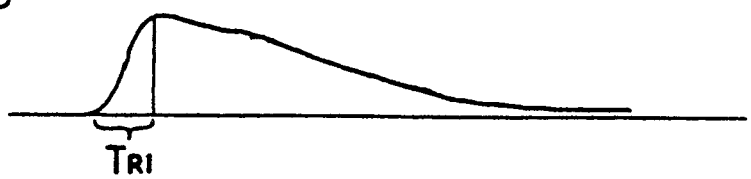
FIG. 3A and FIG. 3B are graphs of output signals from the scintillated light.
Figure 3:
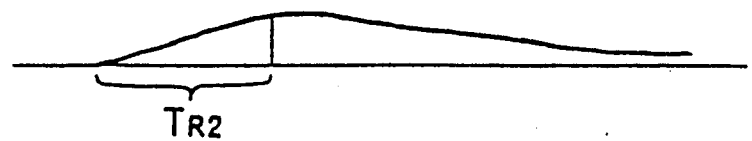

Referring to FIG. 3, the white X-rays 2 are emitted from the X-ray tube 1 by means of the stabilized power source 3 upon applying an appointed voltage to the X-ray tube 1. The white X-rays 2 are turned into pleochromatic secondary X-rays 5 having two wavelengths by passing through the X-ray filter 4. The secondary X-rays 5 are turned into a beam-flux having a suitable diameter by means of the primary collimator 6 to be incident upon the object to be measured 9 supported by the support 7.

From the secondary X-rays 5 incident upon the object to be measured 9, the transmitted X-rays 11, traveling straight, while being subject to absorption by the bone 8, are incident upon the NaI (Tl) scintillator 14 in the X-ray detector 13. The diffracted X-rays 12, diffracted by any crystalline structure in the bone 8, are incident upon the CsI (Tl) scintillator 15. The transmitted X-rays 11, incident upon the scintillator 14, and the diffracted X-rays 12 incident upon the scintillator 15, are converted into a current signal in the photo multiplier 16. This current signal is converted into a pulse-like voltage signal in the preamplifier 17 to be put out as the detected output of the X-ray detector 13.

The scintillation light for the X-rays 11, incident upon the NaI (Tl) scintillator 14, is different from that for the X-rays 12, incident upon the CsI (Tl) scintillator 15, in decay times. That is, 230 to 250 nanoseconds for the NaI (Tl) scintillator 14, and 1000 to 1100 nanoseconds for the CsI (Tl) scintillator 15, so that the detected output of the X-ray detector 13 for the X-rays 11 is different from that for the X-rays 12 in rise time and thus results in the wave-shape as is shown in FIGS. 3(A), 3(B), respectively. Note, the decay times of the scintillator correspond to the rise times of the preamplifier output signals so that the rise times in FIGS. 3A and 3B are induced from the decay times of scintillation light from NaI (T1) and CsI (T1).

Referring to FIGS. 3(A), 3(B), $T_{R1}$, $T_{R2}$ represents a rise time, which amounts to 230 to 250 nanoseconds and 1000 to 1100 nanoseconds, respectively. Accordingly, the transmitted X-rays 11 and the diffracted X-rays 12 can be separated (in a system comprising the counting circuit 21 and the operating circuit 23), based on their rise time, and simultaneously determined by discriminating them in the wave shape-discriminating circuit 19, counting them in the appropriate counting circuits 20, 21 and operating upon them in the operating circuits 22, 23.

The counted value of the transmitted X-rays 11 expresses the bone mineral density. In addition, the diffracted X-rays 12 express the bone strength because they are diffracted by a crystalline surface of the bone 8. Therefore, according to the above described method, both the bone mineral density and the bone strength can be separately and simultaneously measured in a reliable manner.

In the above described preferred embodiment, the constituent members 1, 4, 6, 10, and 13, other than the support 7, are also adapted to be movable in a horizontal direction by means of a scanning drive mechanism (not shown), so that the bone mineral density and bone strength in the respective portions of the object can be measured. Thus, when the present invention is applied to an apparatus for diagnosing osteoporosis, the bone mineral density and the bone strength in the body of a patient can be accurately detected without moving the patient. Not only can such a diagnosis be easily achieved, but also its reliability can be improved.

Figure 4:
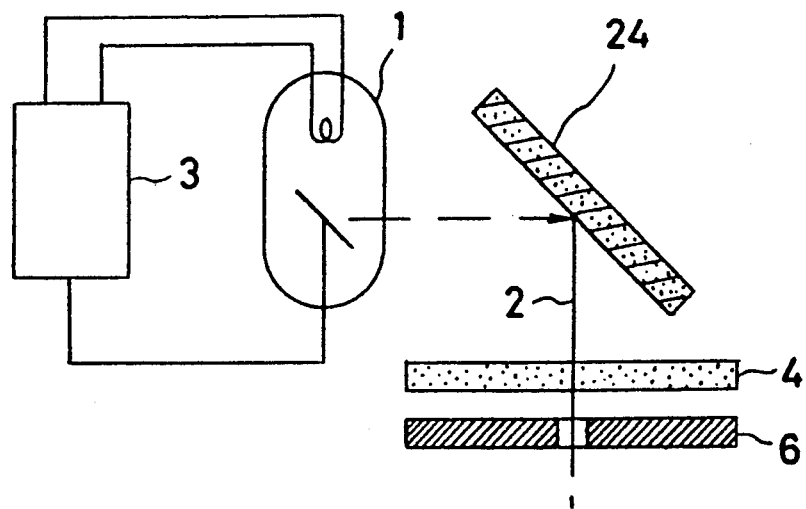
FIG. 4 is a schematic of an alternative embodiment.
Figure 5:
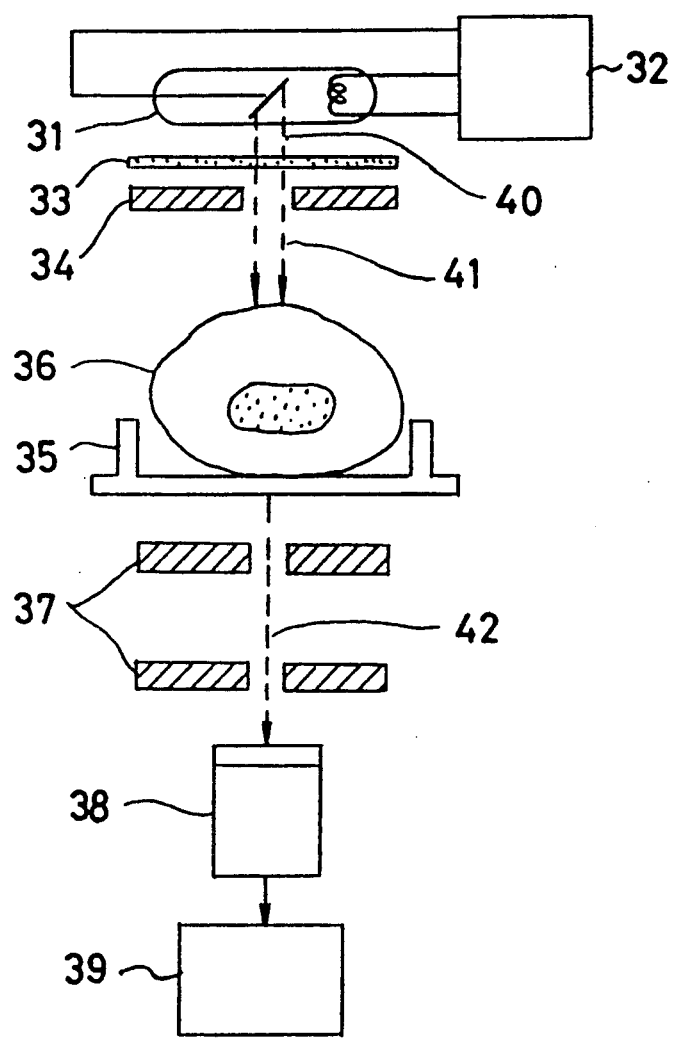
FIG. 5 is a schematic of a prior art apparatus.

The present invention is not limited to the above described preferred embodiment. For example, the X-ray filter 4 may contain many elements and numerous monochromatic secondary X-rays, having three or more wavelengths could be obtained from the X-ray filter. In addition, as shown in FIG. 4, a secondary target 24, containing three or more types of elements, may be arranged at a position where the X-ray tube 1 is positioned in the preferred embodiment shown in FIG. 1, so as to be inclined at almost 45°. The X-ray tube 1 may be arranged almost parallel to the incident direction of the secondary X-rays 2 to create numerous separate monochromatic secondary X-rays, having three or more wavelengths. Factors of error can be accurately eliminated and thus an accurate measurement can be achieved.

In the X-ray detector assembly 13, the NaI (Tl) scintillator 14 and the CsI (Tl) scintillator 15 may be concentrically arranged in a positional relationship opposite to that shown in FIG. 2. Additionally, a semiconductor detector other than the above described scintillator may be used so that the transmitted X-rays 11 and the diffracted X-rays 12 may be simultaneously incident.

As described above, according to the present invention, the transmitted X-rays and the diffracted X-rays can be discriminately measured, so that the bone mineral density and the bone strength can be separately and simultaneously measured so that the diagnosis of osteoporosis can be remarkably improved in accuracy.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A method of measuring bone mineral density and bone strength in a single operation comprising:
   applying a stream of X-rays from a source to a target capable of generating pleochromatic X-rays;
   forming the pleochromatic X-rays into a measurement beam having an optical axis;
   applying the measurement beam to a bone target;
   measuring the X-rays transmitted through the bone target along the optical axis to provide a first measurement signal;
   measuring the X-rays diffracted off of the optical axis simultaneously with the measurement of the first measurement signal to provide a second measurement signal;
   discriminating between the first and second signals on the basis of their wave shape;
   processing the first measurement signal to provide an indication of bone mineral density, and
   processing the second measurement signal to provide an indication of bone strength.

2. The method of claim 1 including a multi-element detector and wherein the wave shape is dependent on decay times of the respective elements of the detector.

3. The method of claim 1 further including counting the incidents of first and second signals.

4. The method of claim 1 wherein the formation of the pleochromatic X-rays is at a 90° angle to the applied stream of X-rays.

5. The method of claim 1 further including collimating the transmitted X-rays into a first stream of X-rays along the optical axis and a second stream of X-rays off of the optical axis.

6. The method of claim 1 further including measuring the X-rays with a scintillation counter.

7. An apparatus for the simultaneous measurement of bone mineral density and bone strength comprising:

a source of X-rays; means for generating pleochromatic X-rays from the same;

means for forming the pleochromatic X-rays into a measurement beam on a predetermined size having an optical axis;

a measurement station for supporting a target area of a patient's body for contact the measurement beam;

means for collimating the transmitted pleochromatic X-rays through the target area into a first beam along the optical axis and a second beam off of the optical axis;

an X-ray detector assembly having a pair of scintillator elements that provide characteristic luminescent light outputs when contacted by X-rays for respectively measuring the first and second beams;

a scintillation counter for providing an electrical signal of the luminescent light;

a wave discriminating circuit for distinguishing the electrical signal of the first beam from the second beam;

means for measuring the impact of the first beam on its scintillator element;

means for measuring the impact of the second beam on its scintillator element;

means for processing the measurement of the first beam to provide an indication of bone mineral density, and means for processing the measurement of the second beam to provide an indication of bone strength.

8. The apparatus of claim 7 wherein the means for collimating includes a pair of apertured plates.

9. The apparatus of claim 7 wherein the detector assembly includes a central scintillator detector element and an annular ring scintillator detector element encompassing the central detector element.

10. An apparatus for the simultaneous measurement of bone mineral density and bone strength comprising:
a source of X-rays;

means for generating pleochromatic X-rays from the source;

means for forming the pleochromatic X-rays into a measurement beam having an optical axis;

a measurement station for supporting a target area of a patient's body for contact with the measurement beam;

means for collimating the transmitted pleochromatic X-rays through the target area into a first beam along the optical axis and a second beam off of the optical axis including a pair of apertured plates;

means for measuring the first beam;

means for measuring the second beam;

means for processing the measurement of the first beam to provide an indication of bone mineral density, and means for processing the measurement of the second beam to provide an indication of bone strength wherein the means for measuring the first beam and the means for measuring the second beam include a detector assembly, having two scintillator detector elements that provide characteristic luminescent light.

11. The apparatus of claim 10 wherein the means for measuring the first beam and the means for measuring the second beam include a scintillation counter and a wave-shape discriminator circuit and means for counting the discriminated wave patterns.

12. The apparatus of claim 11 wherein the detector assembly includes a central scintillator detector element and an annular ring scintillator detector element encompassing the central detector element.

* * * * *